United States Patent [19]

Demarinis et al.

[11] Patent Number: 4,683,229
[45] Date of Patent: Jul. 28, 1987

[54] 6-HALO-9-ALKENYLENEOXY-3-ALKYL-2,3,4,5-TETRAHYDRO-(1H-3)-BENZAZEPINES AND THEIR USE AS SELECTIVE ALPHA-ADRENERGIC RECEPTOR ANTAGONISTS

[75] Inventors: Robert M. Demarinis, Ardmore, Pa.; Francis R. Pfeiffer, Cinnaminson, N.J.

[73] Assignee: SmithKline Beckman Corporation, Philadelphia, Pa.

[21] Appl. No.: 840,621

[22] Filed: Mar. 17, 1986

[51] Int. Cl.[4] .................. C07D 223/16; A61K 31/55
[52] U.S. Cl. ..................................... 514/213; 540/594
[58] Field of Search ................ 260/239 BB; 540/594; 514/213

[56] References Cited

U.S. PATENT DOCUMENTS 3,686,167  8/1972  Fujimura et al. ............. 260/239 BB
3,752,892  8/1973  Hoegerle et al. ............. 260/239 BB
4,192,872  3/1980  Weinstock .................... 260/239 BB
4,465,677  7/1984  DeMarinis et al. ................ 424/244
4,469,634  9/1986  DeMarinis .......................... 260/239

OTHER PUBLICATIONS

DeMarinis, R. M., et al., *J. Med. Chem.* 27, 918 (1984).

Primary Examiner—Richard L. Raymond
Assistant Examiner—D. B. Springer
Attorney, Agent, or Firm—Vincent L. Fabiano; Stuart R. Suter; Alan D. Lourie

[57] ABSTRACT

Selective alpha-adrenoceptor antagonists having the Formula:

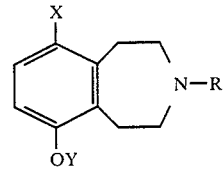

which are useful to produce alpha$_3$-selective adrenoceptor antagonism, pharmaceutical compositions including these antagonists, and methods of using these antagonists to selectively antagonize alpha$_3$ adrenoceptor mediated activity in mammals.

11 Claims, No Drawings

6-HALO-9-ALKENYLENEOXY-3-ALKYL-2,3,4,5-TETRAHYDRO-(1H-3)-BENZAZEPINES AND THEIR USE AS SELECTIVE ALPHA-ADRENERGIC RECEPTOR ANTAGONISTS

FIELD OF THE INVENTION

This invention relates to novel 6(9)-substituted-3-benzazepines that are selective alpha-adrenergic receptor antagonists.

BACKGROUND OF THE INVENTION

The autonomic nervous system is separated into the cholinergic and adrenergic nervous systems. Norepinephrine, the neurotransmitter of the adrenergic nervous system, exerts its activity by interaction with receptors (adrenoceptors) on the effector organs or on the nerve endings. The adrenoceptors are of two primary types: alpha and beta. Further, based upon the selectivity of the receptors for a series of agonists and antagonists, the alpha adrenoceptors are divided into $alpha_1$ and $alpha_2$ subtypes.

$Alpha_1$ adrenoceptors are those positioned on the effector organ, thus $alpha_1$ stimulation produces a pharmacologic effect. $Alpha_2$ adrenoceptors first were discovered on alpha-adrenergic nerve endings. These prejunctional $alpha_2$ adrenoceptors are involved in the regulation of neurotransmitter release through a negative feedback mechanism mediated by the neurotransmitter.

A large amount of experimental evidence now supports the view that there is a heterogeneous class of alpha receptors which mediates vasoconstriction in the vasculature of the pithed rat and pithed cat. (For a general review see Timmermans and Van Zwieten, *J. Med. Chem.*, 25, 1389 (1982).) Experiments using selective agonists and antagonists of both $alpha_1$ and $alpha_2$ receptors demonstrated that in addition to the classical postjunctional $alpha_1$ receptor, an additional postjunctional receptor was present which closely resembled the prejunctional $alpha_2$ adrenoceptor which had been characterized in many systems. The concept of postjunctional $alpha_2$ adrenoceptors mediating prazosin-resistant vasoconstriction therefore was proposed (Timmermans, et al., *Naunyn-Schmedeberg's Arch. Pharmacol.*, 310, 189 (1979), Ruffolo, *Pharm. Biochem. and Behav.*, 22, 827 (1985).) Additional evidence suggests that these receptors are located extra-synaptically, and are activated primarily by circulating catecholamines as opposed to neuronally released norepinephrine which primarily activates the $alpha_1$ adrenoceptor (Yamaguchi and Kopin, *J. Pharm. Exp. Ther.*, 214, 275 (1980)). It has now been discovered that the prazosin-insensitive postjunctional $alpha_2$ receptor is pharmacologically distinct from the prejunctional $alpha_2$ receptor and hereafter this postjunctional, prazosin-insensitive receptor shall be referred to as the $alpha_3$ adrenoceptor.

As one of the primary regulators of peripheral vascular tone, alpha adrenoceptors long have been the targets of efforts to develop effective antihypertensive agents. These efforts have resulted in several compounds that interact selectively with $alpha_1$ or $alpha_2$ receptors. Selective agonists include phenylephrine and methoxamine which preferentially activate $alpha_1$ receptors; and clonidine, alpha-methylnorepinephrine, and tramazoline which selectively activate $alpha_2$ receptors. Examples of selective alpha-adrenoceptor antagonists include prazosin which has high selectivity for $alpha_1$ adrenoceptors; and the $alpha_2$-selective blockers yohimbine and rauwolscine. Absent from the therapeutic armamentarium are selectve agonists and antagonists of $alpha_3$ vis-á-vis $alpha_2$ adrenoceptors.

Based on the distribution and function of $alpha_3$ adrenoceptors it is clear that compounds having selective affinity for $alpha_3$ vis-á-vis $alpha_2$ adrenoceptors (hereafter referred to as $alpha_3$ selective) would be important additions to the agents available in treating cardiovascular disease. $Alpha_3$ adrenoceptors have been found in spontaneously hypertensive rats (Medgett and Langer, *J. Pharmacol. Exp. Ther*, 231, 159 (1984)) and to play a role in the maintenance of blood pressure in essential hypertension (Bolli, et al., *Journal of Hypertension*, 1985. Prazosin-insensitive alpha-adrenergic ($alpha_3$) contractile mechanisms also have been found on human digital arteries and veins. Stevens, M. J. and Moulds, R. F. W., *J. Cardiovasc. Pharmacol*, 4:S129–S133 (1982). In animals and man there is evidence for increased activation of $alpha_3$ receptors in the hypertensive state. Because the $alpha_3$ adrenoceptor is unaffected by the $alpha_1$ antagonists presently available for clinical use, blockade of vasoconstriction mediated by circulating catecholamines which act on $alpha_3$ receptors offers a novel approach to adrenolytic therapy in hypertension.

Further, reflex tachycardia is a frequent and severe adverse effect encountered when utilizing available alpha-adrenoceptor antagonists in the treatment of hypertension. This adverse effect is mediated by enhanced norepinephrine release by the nerves that innervate the cardiac pacing tissues which is a cumulative effect of the reduction in systemic blood pressure produced by $alpha_1$ adrenoceptor blockade and the disruption of feedback inhibition of norepinephrine release resulting from $alpha_2$ blockade. Thus, because selective $alpha_3$ antagonists leave $alpha_2$ adrenoceptors free to participate in feedback inhibition of norepinephrine release, antihypertensive therapy with these agents will be associated with a lesser incidence and lower frequency of tachycardia.

The cardiovascular diseases for which $alpha_3$ selective antagonists are useful are not limited to hypertension. $Alpha_3$ receptors are present on coronary arteries (Holtz, et al., *Eur. J. Pharm.*, 82, 199 (1982)); as in the canine saphenous vein, the coronary artery $alpha_3$ adrenoceptors may be innervated. Thus, an $alpha_3$-selective antagonist would be an effective coronary blood vessel dilator thereby increasing blood flow and alleviating symptoms of cardiac hypoxia such as angina pectoris. Additionally, blockade of $alpha_3$ adrenoceptors, alone or in combination with $alpha_1$ adrenoceptor blockade, also reduces cardiac preload and afterload thereby enhancing cardiac function in cardiomyopathic diseases such as congestive heart failure. In addition to agents employed in the treatment of cardiovascular diseases, $alpha_3$-selective antagonists will make possible further characterization of the adrenergic nervous system to enable identification of other disease states in which treatment with these agents will be of therapeutic benefit.

U.S. Pat. No. 4,469,634, dated Sept. 4, 1984, describes allyloxy- and allythio-2,3,4,5-tetrahydro-1H-3-benzazepines useful as intermediates for preparing $alpha_2$ adrenoceptor affinity resins and as antihypertensive agents. Included in the compounds disclosed in this reference is 9-allyloxy-6-chloro-3-methyl-2,3,4,5-tetrahydro-1H-3- benzazepine hydrochloride. As is demonstrated below, despite its structural similarity to 9-(3-methyl-2-butenyloxy)-6-chloro-3-methyl-2,3,4,5-tetrahydro-1H-3 benzazepine, an alpha₃ selective antagonist of the present invention, the alpha₃ selectivity of the reference compound does not approach the high degree of specificity exhibited by the presently invented compounds.

SUMMARY OF THE INVENTION

The invention resides in the discovery that various 6(9)-substituted-3-benzazepine compounds are alpha₃-selective antagonists. Presently preferred compounds of the invention include:

9-(3-methyl-2-butenyloxy)-6-chloro-3-methyl-2,3,4,5-tetrahydro-1H-3-benzazepine; and 9-(1-propenyloxy)-6-chloro-3-methyl-2,3,4,5-tetrahydro-1H-3-benzazepine.

In a further aspect of the invention there is provided a method of producing alpha₃-selective antagonism in mammals, including humans, that comprises administering internally to a subject an effective amount of a 6(9)-substituted-3-benzazepine compound.

Included in the present invention are pharmaceutical compositions for producing alpha₃-selective antagonism that contain compounds useful in the method of the invention and a pharmaceutical carrier.

DETAILED DESCRIPTION OF THE INVENTION

The presently invented compounds that are alpha₃-selective antagonists have the following formula:

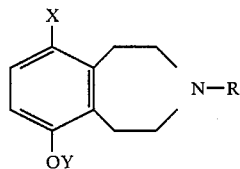

Formula (I)

in which:
R is $C_{1-5}$ alkyl;
X is Br, Cl, F;
Y is —$CH_2$—CH=C($CH_3$)$_2$, —CH=CH—$CH_3$, —$CH_2$—$\overset{CH_3}{\underset{|}{C}}$=$CH_2$, —CH=C($CH_3$)$_2$, —CH=CH—$CH_2$—$CH_3$, or —CH=CH—CH($CH_3$)$_2$; or any pharmaceutically acceptable salt or hydrate thereof.

The compounds of Formula I are prepared from corresponding 6-halo-9-hydroxy-2,3,4,5-tetrahydro-1H-3-benzazepines by known processes such as shown below wherein R, X, and Y are as described in Formula (I).

Scheme I

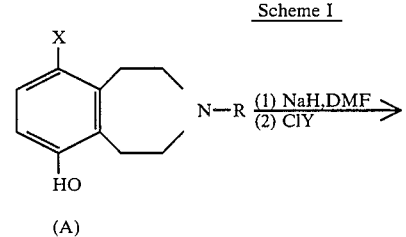

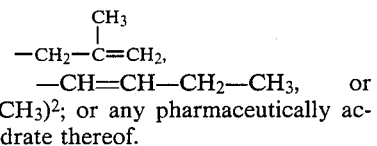

-continued
Scheme I

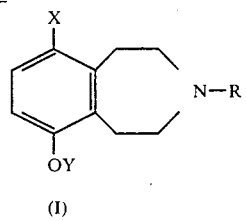

(I)

The starting 6-halo-9-hydroxy-2,3,4,5-tetrahydro-1H-3-benzazepines are known and described in published references, such as *J. Med. Chem.*, Vol. 27, pp. 918–921 (1984), or can be obtained readily. In the process illustrated above, the starting compounds (A) first are added to a suitable base such as an alkali metal hydride, for example, sodium hydride, in a suitable organic solvent such as dimethylformamide. Thereafter, a selected alkenyl halide, for example an alkenyl chloride, is added to the mixture containing compound (A) to produce 6-halo-9-alkenyloxy-3-methyl-2,3,4,5-tetrahydro-1H-3-benzazepine compounds of Formula (I).

The alkyl substituent (R) at the 3-position of the Formula (I) compounds includes $C_1$ alkyl, $C_2$ alkyl, $C_3$ alkyl, $C_4$ alkyl and $C_5$ alkyl whether straight chain or branched. Formula (I) compounds having a desired alkyl substituent at the 3-position are prepared from Formula (A) compounds appropriately substituted at the 3-position.

The alkenyl halides used in the process of Scheme I are known and described in published references or can be obtained readily. The alkenyl halide used in making compounds of this invention is selected so that the alkenyl group is the same as that desired to be present on the oxygen at the 9-position of the particular compound being prepared. Alternatively, the alkenyl group of the alkenyl halide has a double bond in a position other than that desired and the compound of the invention is produced by rearrangement of the double bond in the presence of an alkoxide such as potassium tert butoxide.

The pharmaceutically acceptable, nontoxic, acid addition salts having the utility of the free bases of Formula (I), prepared by methods well known in the art, are formed with inorganic or organic acids, for example maleic, fumaric, benzoic, ascorbic, pamoic, succinic, bismethylenesalicylic, methanesulfonic, ethane disulfonic, acetic, propionic, tartaric, salicylic, citric, gluconic, aspartic, stearic, palmitic, itaconic, glycolic, p-aminobenzoic, glutamic, benzenesulfonic, hydrochloric, hydrobromic, sulfuric, cyclohexylsulfamic, phosphoric and nitric acids.

Because the compounds of Formula (I) are alpha-adrenoceptor antagonists they have therapeutic value in the treatment of cardiovascular diseases such as hypertension and coronary hypoxia resulting from occluded blood vessels and in the treatment of other disease states that are ameliorated by alpha adrenoceptor antagonism, such as benign prostatic hypertrophy.

The compounds of this invention, however, are unlike prior available alpha-adrenoceptor antagonists. The invented compounds are the first known compounds that selectively antagonize alpha₃ adrenoceptors vis-á-vis alpha₂ adrenoceptors. As such these compounds will be effective antihypertensive agents that are associated with diminished or absent adverse effects related to alpha₂-adrenoceptor antagonism, such as reflex tachycardia. The alpha₃ adrenoceptor selectivity of these compounds was particularly suprising and unexpected because a compound closely related in structure to those of the present invention, 9-allyloxy-6-chloro-3-methyl-2,3,4,5-tetrahydro-1H-3-benzazepine hydrochloride, referenced above, possesses insignificant alpha₃-adrenoceptor selectivity.

The alpha-adrenoceptor selectivity of certain compounds of the present invention and the prior art compound, 9-allyloxy-6-chloro-3-methyl-2,3,4,5-tetrahydro-1H-3-benzazepine hydrochloride, was determined using the following in vitro systems.

Alpha₁ activity was determined using the rabbit aorta. Male New Zealand White rabbits (2–4 Kg) were euthanized by cervical concussion. A 4 cm portion of the thoracic aorta was removed and placed in a dish of cold (10° C.) Krebs-Hensleit solution. The tissue was cleaned of fat and connective tissue and cut into segments of approximately 3 mm in length. These segments were suspended in 10 ml tissue baths via hangers constructed of 0.25 mm tungsten wire. One hanger was fixed to a support in the bath, the other attached via silk thread to a force-displacement transducer.

Tissue segments were equilibrated for 2 hours prior to drug testing, during which time basal tension was maintained at 2 gm. Tissues were washed at 30 minute intervals during this equilibration period. The Krebs-Hensleit solution contained cocaine (6 $\mu$M) to block neuronal uptake and propranolol (1 $\mu$M) to block beta-adrenoceptors. Tissues were usually challenged once with norepinephrine (0.1 $\mu$M) during the equilbration period to check for viability.

A cumulative concentration-response curve to norepinephrine was obtained in each aortic segment. Following washout of norepinephrine, the alpha adrenoceptor antagonist to be tested was added to the bath. After the tissue had been in contact with the antagonist for 30–60 minutes, the norepinephrine concentration response-curve was repeated in the presence of antagonist. The tissue was then washed again, and a tenfold higher concentration of antagonist added. Following equilibration (30–60 minutes), a third norepinephrine concentration-response curve was determined in the presence of the antagonist.

The receptor dissociation constant ($K_B$) for the antagonist was determined using the relationship $$K_B = \frac{\text{Antagonist Concentration}}{\text{Dose Ratio} - 1}$$

(Furchgott, R. F., *Handbook of Experimental Pharmacology*, eds. Eichler, et al., pp. 283–335 (Springer 1972)). The $K_B$ value obtained at each antagonist concentration was averaged to obtain a mean $K_B$ for each experiment.

One of the two systems employed to determine alpha₂ activity of the compounds was the isolated, superfused guinea pig left atrium. Briefly, the heart is removed from a pentobarbital-anesthetized male guinea pig. The left atrium is separated, dissected free of extraneous tissue and mounted in a 2 ml superfusion chamber. The tissue is paced at 60 pulse/minute and the sympathetic nerves excited at 6 minute intervals by field stimulation. The response to nerve stimulation is measured as the difference in contractile force between the basal contraction and peak contraction following a nerve stimulation. A concentration-response curve for clonidine (a known alpha₂ antagonist) is prepared by administering increasing concentrations of clonidine following each successive stimulation. The tissue then is superfused for thirty minutes with the alpha-adrenoceptor antagonist to be tested and the clonidine concentration-effect curve is repeated in the presence of antagonist. Data are reported as $K_B$, defined above. Additional details of this test system are found in Hieble, J. P. and R. G. Pendleton, *Arch. Pharmacol.*, 309:217–224 (1979).

The second system utilized in determining the alpha₂ activity of the compounds of interest is the isolated, superfused guinea pig vas deferens (Vas Def). From male (300–600 g) guinea pigs sacrificed by administration of a lethal amount of pentobarbital, both vasa deferentia were removed and placed in a dish containing a cold nutrient-buffer solution. The tissue was cleaned and the fibrous sheath removed gently. The ends were trimmed to yield segments about 4 cm in length and 4-0 silk ties attached to each end. The vasa deferentia then were incubated in 10 ml of nutrient-buffer solution containing 75 Ci of $^3$H-norepinephrine. Tissue was incubated at 37° C. for 30 minutes with continuous gassing with 95% $O_2$, 5% $CO_2$. After incubation, the tissue was mounted in a superfusion apparatus constructed of 3 mm ID glass tubing. One end was connected, via the silk tie, to a plug constructed of silicone rubber and polyethylene with a platinum wire hook. The other tie was connected to a force-displacement transducer. About 1 g of tension was applied to the tissue, and superfusion with nutrient-buffer solution initiated at 2 ml/minute, using a peristaltic pump. The chambers had platinum electrodes fused through the glass at the top and bottom to allow field stimulation of the tissue.

Before compound testing, tissues were equilibrated for at least 2 hours, during which time stimulation (3 Hz, 0.7 msec pulse duration, 80 V) was applied for 2 minutes at 30 minute intervals. Following this equilibration period, three control stimulations were performed. For each stimulation, two effluent samples were collected directly into 20 ml scintillation vials; one prior to, and one during field stimulation. The basal sample was collected during a 2 minute interval immediately prior to stimulation. The stimulation sample was collected beginning 30 seconds after initiation of stimulation, and continuing for 30 seconds following termination of the field stimulation. This lag period is to allow for the dead space in the superfusion chamber. This collection-stimulation procedure was repeated at 20 minute intervals. Following the third control collection, compound was added into the superfusion flow; 20 minutes later the collection-stimulation was repeated in the presence of compound. Compound concentration was increased ten-fold following each stimulation, and the cycle repeated until four drug concentrations had been tested. A final stimulation-collection was performed after termination of compound superfusion.

Ten ml of standard scintillation fluid (Aquasol-II) was added to all samples, and the DPM values were determined on a beta-scintillation counter. The stimulated/basal release ratio was determined for each pair. The stimulated/basal ratios for the three initial control collections were averaged to obtain a mean control ratio. The compound effect was determined by comparing the stimulated/basal ratio in the presence of increasing compound concentration to the mean control ratio. The $EC_{50}$ was defined as the compound concentration producing a 50% increase in the stimulated/basal release ratio.

The dog saphenous vein (DSV) was used as the test system for measuring activity of the compounds at the alpha₃ receptor. This test system has been shown a suitable preparation in which to characterize postsynaptic alpha₂ (alpha₃) adrenoceptors. Sullivan, A. T. and G. M. Drew, *Arch. Pharmacol.* 314:249-58 (1980). This test system is prepared by removing the lateral saphenous vein from an anesthetized dog and cutting the vein into segments of 10 mm in length. Each segment then is cut into a helical strip and mounted, in a tissue bath, between a stationary tissue holder and transducer with which isometric contractions are recorded as changes in grams of tension. Additional details of this methodology are found in Fowler, P. J., et al., *J. Pharmacol. Exp. Ther.* 229:712-18 (1984).

The alpha₃ activity of the compounds of interest is determined by measuring shifts in the dose-response curve of a specific agonist induced by the tested compounds. The alpha₂ specific agonist, BHT-920, was used in testing the compounds listed in Table I. Data are reported as $K_B$, defined above.

Table 1 shows the alpha-adrenoceptor activity of the tested compounds in the experimental systems employed. The results are expressed in nanomolar concentrations. Compound (D) is the prior art compound mentioned above; compounds (E) and (F) are compounds of the present invention.

TABLE I

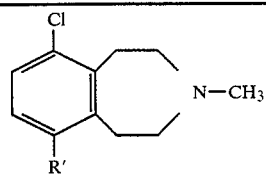

| Compound | R' | $K_B$ alpha₁ Aorta | $K_B$ alpha₂ Atrium | $EC_{50}$ alpha₂ Vas Def | $K_B$ alpha₃ DSV |
|---|---|---|---|---|---|
| (D) | O—CH₂—CH=CH₂ | 150 | 903 | 224 | 54 |
| (E) | O—CH₂—CH=C(CH₃)₂ | 150 | >10,000 | >10,000 | 37 |
| (F) | O—CH=CH—CH₃ | 31 | >1,000 | >10,000 | 100-200 |

The data in Table 1 establish that the alpha₃ vis-á-vis alpha₂ activity of compounds E and F is markedly different from that of the prior art compound, D. In both systems employed to measure alpha₂ activity, compound D exhibited significant activity at the alpha₂ receptor. Comparing the results obtained in the guinea pig vas deferens and the dog saphenous vein shows that compound D produced an alpha₂ effect at concentrations only four times those required to produce an alpha₃ effect. So small a difference is unlikely to be significant in vivo. In contrast, the two tested compounds of the invention, E and F, produced no alpha₂ effects at the highest tested concentration in either the guinea pig atrium or guinea pig vas deferens and yet were potent antagonists in the alpha₃ test system. For example, comparing the guinea pig vas deferens and dog saphenous vein data for compound E shows at least a 200 fold separation in the concentrations producing alpha₂ and alpha₃ effects as contrasted with the four fold difference in these concentrations observed with compound D. Given that compound E differs from D only by two methyl groups and compound F differs from D only in the position of the double bond, and that the alpha₁ activity of these compounds is similar, these results were particularly surprising and unexpected.

Further, spontaneously hypertensive rats were dosed, intravenously, at a dose of 1.5 mg/kg, with a solution of one of the compounds of the invention (Compound E, Table I) and mean arterial blood pressure was monitored for 45 minutes using indwelling cannulae positioned in the tail arteries. At the end of the 15 minute infusion, systolic and diasystolic pressures had reached their nadirs and were each approximately 30 to 35 mm Hg below vehicle-treated controls. Thirty minutes following cessation of the infusion, systolic and diasystolic pressures remained approximately 20 mm Hg less than the controls. Also, heart rate was measured during the period blood pressure was monitored. No statistically significant reflex tachycardia was observed even though substantial blood pressure reductions were produced.

The compounds can be incorporated into convenient dosage forms such as capsules, tablets, or injectable preparations. Solid or liquid pharmaceutical carriers can be employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid, or an aqueous or nonaqueous liquid suspension or solution.

The pharmaceutical preparations are made following conventional techniques of a pharmaceutical chemist involving mixing, granulating and compressing, when necessary, for tablet forms, or mixing, filling, and dissolving the ingredients, as appropriate, to give the desired oral or parenteral products.

Doses of the present compounds in a pharmaceutical dosage unit will be an efficacious, nontoxic quantity selected from the range of 0.01-100 mg/kg of active compound, preferably 0.1-50 mg/kg. The selected dose is administered to a human patient in need of treatment from 1-6 times daily, orally, rectally, by injection, or continuously by infusion. Parenteral administration, which uses lower dosages, is preferred. Oral administration, at higher dosages, however, also can be used when safe and convenient for the patient.

The following examples are illustrative of preparation of Formula I compounds. The examples are not intended to limit the scope of the invention as defined hereinabove and as claimed below.

EXAMPLE 1

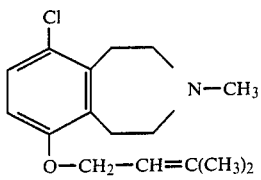

9-Hydroxy-6-chloro-3-methyl-2,3,4,5-tetrahydro-1H-3-benzazepine (3.0 g, 0.0142 mol) was added to 1.8 g of potassium hydride (37%, 0.0166 mol) suspended in 5 ml dry dimethylformamide and chilled in an ice bath. The mixture was stirred magnetically at room temperature for 45 minutes, at which time it was a deep cherry red solution. A solution of 3-methyl-1-bromo-2-butene (2.2 g, 97%, 0.0142 mol) in 5 ml of dry dimethylformamide was added dropwise rapidly and the mixture was heated to 55° C. for six hours. The resulting opaque, pink mixture was poured onto 100 ml ice, and the crude product was extracted with ethyl acetate, washed with brine, and dried over magnesium sulfate, filtered and evaporated to 4.6 g of brown oil. The oil was chromatographed on a flash silica column, eluting with 5% methanol and 0.25% ammonium hydroxide in ethyl acetate to give 1.9 g of oil, which solidified. The maleate salt was prepared by combining 1.06 g (0.00379 mol) in 5 ml ether with 0.46 g (0.00397 mol) of maleic acid in 20 ml of ether. A crystalline precipitate formed immediately, m.p. 149.5°–151° C. Recrystallization from acetonitrile gave 1.06 g 9-(3-methyl-2-butenyloxy)-6-chloro-3-methyl-2,3,4,5-tetrahydro-1H-3-benzazepine maleate, m.p. 165°–165.6° C.

EXAMPLE 2

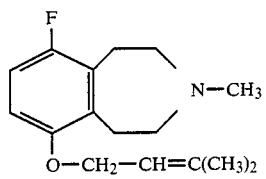

The process of Example 1 using 9-hydroxy-6-fluoro-3-methyl-2,3,4,5-tetrahydro-1H-3-benzazepine in place of the 6-chloro analogue yields 9-(3-methyl-2-butenyloxy)-6-fluoro-3-methyl-2,3,4,5-tetrahydro-1H-3-benzazepine.

EXAMPLE 3

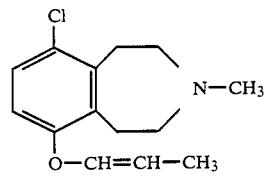

The process of Example 1 for producing the free base using 1-bromo-2-propene in place of 3-methyl-1-bromo-2-butene yields 9-allyloxy-6-chloro-3-methyl-2,3,4,5-tetrahydro-1H-3-benzazepine. To potassium tert butoxide (290 mg, 2.6 moles) dissolved in 3 ml of dimethylsulfoxide was added 9-allyloxy-6-chloro-3-methyl-2,3,4,5-tetrahydro-1H-3-benzazepine (378 mg, 1.5 mmole) dissolved in 3 ml of dimethylsulfoxide. This mixture was heated at 100° C. for 2½ hours, and then poured into 50 ml of ice and extracted with methylene chloride. The methylene chloride solution was washed with 60 ml of water in ten portions followed by drying over sodium sulfate and potassium carbonate. Filtration and evaporation of the filtrate produced 175 mg of a greenish oil, 42% product by gas chromatograph. Chromatography on a flash silica column, eluting with a gradient of 1–7% methanol in methylene chloride containing 0.35% of concentrated aqueous ammonium hydroxyide yielded 56 mg of pure 9-(1-propenoxy)-6-chloro-3-methyl-2,3,4,5-tetrahydro-1H-3-benazaepine. Treatment with 19 mg of maleic acid in methyl cyanate and ether gave 35 mg of 9-(1-propenoxy)-6-chloro-3-methyl-2,3,4,5-tetrahydro-1H-3-benzazepine maleate, m.p.: 147°–148° C.

EXAMPLE 4

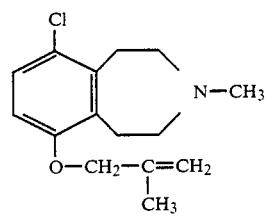

The process of Example 1 using 2-methyl-1-bromo-2-propene in place of 3-methyl-1-bromo-2-butene yields 9-(2-methyl-2-propenyloxy)-6-chloro-3-methyl-2,3,4,5-tetrahydro-1H-3-benzazepine. The process of Example 3 using the prepared 9-(2-methyl-2-propenyloxy)-6-chloro-3-methyl-2,3,4,5-tetrahydro-1H-3-benzazepine yields 9-(2-methyl-1-propenyloxy)-6-chloro-3-methyl-2,3,4,5-tetrahydro-1H-3-benzazepine.

EXAMPLE 5

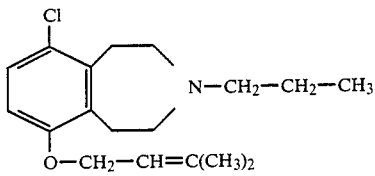

The process of Example 1 using the free base of 9-hydroxy-6-chloro-3-propyl-2,3,4,5-tetrahydro-1H-3-benzazepine in place of 9-hydroxy-6-chloro-3-methyl-2,3,4,5-tetrahydro-1H-3-benzazepine yields 9-(3-methyl-2-butenyloxy)-6-chloro-3-propyl-2,3,4,5-tetrahydro-1H-3-benzazepine.

EXAMPLE 6

An oral dosage form for administering the presently invented compounds is produced by screening, mixing, and filling into a hard gelatin capsule the ingredients in Table III, below.

TABLE III

| Ingredients | Amounts |
| --- | --- |
| 9-(3-methyl-2-butenyloxy)-6-chloro-3-methyl-2,3,4,5-tetrahydro-1H—3-benzazepine | 50 mg |
| magnesium stearate | 5 mg |
| lactose | 75 mg |

EXAMPLE 7

The sucrose, calcium sulfate dihydrate and 6(9)-substituted-3-benzazepine shown in Table IV below, are mixed and granulated with a 10% gelatin solution. The wet granules are screened, dried, mixed with the starch, talc and stearic acid, screened and compressed into a tablet.

TABLE IV

| Ingredients | Amounts |
| --- | --- |
| 9-(2-propenyloxy)-6-chloro-3-methyl-2,3,4,5-tetrahydro-1H—3-benzazepine | 100 mg |
| calcium sulfate dihydrate | 150 mg |
| sucrose | 20 mg |
| starch | 10 mg |
| talc | 5 mg |
| stearic acid | 3 mg |

EXAMPLE 8

1-(3-methyl-2-butenyloxy)-6-fluoro-3-methyl-2,3,4,5-tetrahydro-1H -3-benzazepine maleate, 75 mg, is dispersed in 25 ml of normal saline to prepare an injectable preparation.

While the preferred embodiments of the invention are illustrated by the above, it is to be understood that the invention is not limited to the precise instructions herein disclosed and that the right to all modifications coming within the scope of the following claims is reserved.

What we claimed is:

1. A compound represented by the Formula:

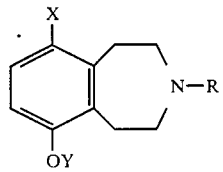

in which:
R is $C_{1-5}$ alkyl;
X is Br, Cl, F;
Y is $-CH_2-CH=C(CH_3)_2$, $-CH=CH-CH_3$, $-CH=C(CH_3)_2$, $-CH=CH-CH_2-CH_3$, or $-CH=CH-CH(CH_3)_2$;
or any pharmaceutically acceptable salt or hydrate thereof.

2. A compound of claim 1 wherein R is $CH_3$.
3. A compound of claim 2 wherein X is Cl.
4. The compound of claim 3 that is 9-(1-propenyloxy)-6-chloro-3-methyl-2,3,4,5-tetrahydro-1H-3-benzazepine.
5. The compound of claim 3 that is 9-(3-methyl-2-butenyloxy)-6-chloro-3-methyl-2,3,4,5-tetrahydro-1H-3-benzazepine.
6. A pharmaceutical composition for producing selective $alpha_3$-adrenoceptor antagonism that comprises an effective amount of a compound of claim 1 and a suitable pharmaceutical carrier.
7. The pharmaceutical composition of claim 6 wherein the compound is 9-(1-propenyloxy)-6-chloro-3-methyl-2,3,4,5-tetrahydro-1H-3-benzazepine.
8. The pharmaceutical composition of claim 6 wherein the compound is 9-(3-methyl-2-butenyloxy)-6-chloro-3-methyl-2,3,4,5-tetrahydro-1H-3-benzazepine.
9. A method of producing selective $alpha_3$-adrenoceptor antagonism in mammals that comprises administering internally to a subject in need of such antagonism an effective amount of a compound of claim 1.
10. The method of claim 9 in which the compound is 9-(1-propenyloxy)-6-chloro-3-methyl-2,3,4,5-tetrahydro-1H-3-benzazepine.
11. The method of claim 9 in which the compound is 9-(3-methyl-2-butenyloxy)-6-chloro-3-methyl-2,3,4,5-tetrahydro-1H-3-benzazepine.

* * * * *